United States Patent [19]

Gordon

[11] Patent Number: 4,530,351
[45] Date of Patent: Jul. 23, 1985

[54] DEVICE FOR PROTECTING THE WEB OF A HAND IN A MEDICAL CAST

[76] Inventor: Eliot Gordon, 2860 S. Ocean Blvd., Palm Beach, Fla. 33480

[21] Appl. No.: 605,140

[22] Filed: Apr. 30, 1984

Related U.S. Application Data

[63] Continuation-in-part of Ser. No. 438,530, Nov. 1, 1982, which is a continuation-in-part of Ser. No. 403,352, Jul. 30, 1982, abandoned.

[51] Int. Cl.³ .................. A61F 13/00; A61F 5/04
[52] U.S. Cl. .......................... 128/82; 128/85; 128/90; 128/87 R; D24/64
[58] Field of Search ............... 128/87 R, 82, 83, 90, 128/85, 89 R; D33/64

[56] References Cited

U.S. PATENT DOCUMENTS

| D. 200,752 | 3/1965 | Hill | D83/1 |
|---|---|---|---|
| 1,174,675 | 3/1916 | Cady et al. | 128/87 R |
| 1,313,344 | 8/1919 | Smart | 128/87 R |
| 2,371,197 | 3/1945 | Taylor | 128/87 R |
| 2,384,804 | 9/1945 | Anderson | 128/83.5 X |
| 3,533,405 | 10/1970 | Collins | 128/77 |
| 3,585,993 | 6/1971 | Heedly | 128/80 |
| 4,143,653 | 3/1975 | Wichman | 128/87 A |
| 4,327,909 | 5/1982 | Neufeld | 272/137 |

OTHER PUBLICATIONS

Orthopaedic Appliances Atlas, J. W. Edwards, vol. 1, 1952, pp. 277, 282, 283, 284, 307, 316, 483.

Primary Examiner—Richard J. Apley
Assistant Examiner—David Isabella
Attorney, Agent, or Firm—Kenway & Jenney

[57] ABSTRACT

In order to prevent inflammation and irritation of the web of a hand contained in a cast there is provided a smooth surfaced U-shaped member fitting into the web of the hand with one leg traversing the palm and the other leg traversing the back of the hand. The U-shaped member is also provided with anchoring means for engaging the material of the cast and adapted to maintain the U-shaped member and the cast in proper position.

2 Claims, 6 Drawing Figures

DEVICE FOR PROTECTING THE WEB OF A HAND IN A MEDICAL CAST

CROSS-REFERENCE TO RELATED APPLICATION

This is a continuation-in-part of my copending application U.S. Ser. No. 438,530 filed Nov. 11, 1982 and entitled Device for Protecting the Web of a Hand in a Medical Cast, which application is a continuation-in-part of U.S. Ser. No. 403,352 filed July 30, 1982, now abandoned.

BACKGROUND OF THE INVENTION

It has been found that when a hand is contained in a medical cast, as, for example, when the patient's wrist has been broken, irritation and inflammation of the skin in the web almost always takes place within a few days and becomes progressively worse with time. Such a cast is generally worn for five to seven weeks, although the period may be considerably longer in cases involving severe fractures.

SUMMARY OF THE INVENTION

The object of this invention is to provide a smooth member of U-shaped configuration adapted to have the base of the U span the web with one leg traversing the palm and the other leg traversing the back of the hand. The U-shaped member is also provided with anchoring means, such as molded or metal flanges, which are adapted to be engaged by and molded into the casting material. The U-shaped member serves to protect the skin of the web from engagement with casting material and thereby prevent irritation and inflammation. The anchoring means serve the primary function of maintaining the cast in proper position. In many cases, there is a swelling beneath the cast and when the swelling is reduced by the passage of time the cast becomes loose. Then the anchoring means prevents the cast from moving upwardly along the wrist and arm and maintains it in proper position. The U-shaped member may conveniently be formed from a fairly resilient rod or cylinder of plastic into which the anchoring flanges are molded or inserted, but the cross-sectional shape of the U-shaped member is not particularly important; it can be an oval or an arcuate cross-section so long as there are no sharp edges and the surface is entirely smooth.

DESCRIPTION OF THE PREFERRED EMBODIMENTS

Figure 1:
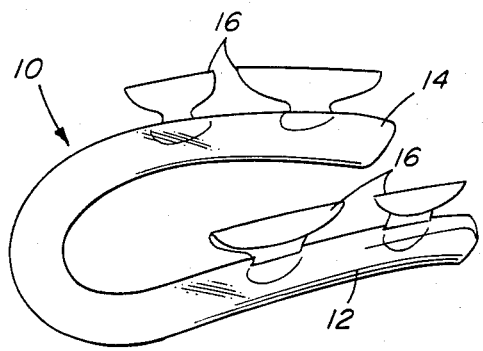
FIG. 1 is a view in perspective of the U-shaped member with its anchoring flanges.
Figure 3:
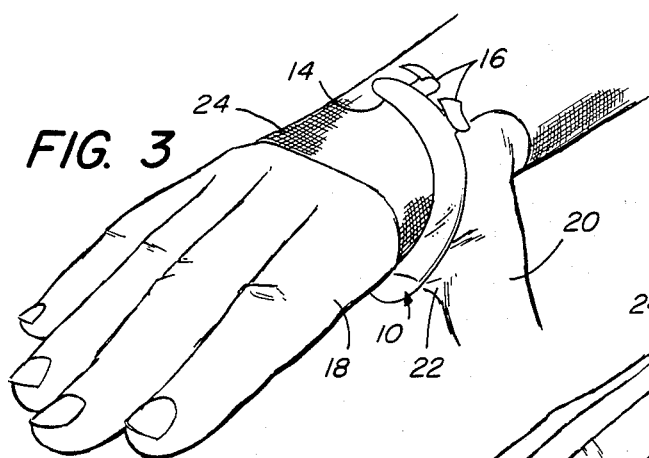
FIG. 3 is a view similar to FIG. 2 illustrating the manner in which one leg of the U-shaped member spans the back of the hand.
Figure 4:
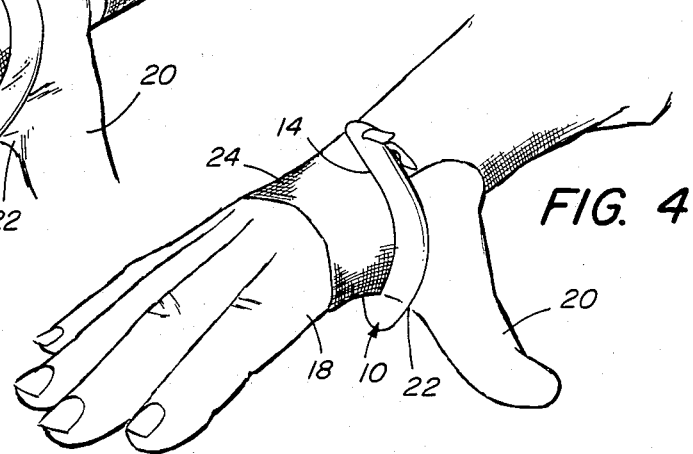
FIG. 4 is a view in perspective similar to FIG. 3.

As shown in FIG. 1, the U-shaped member 10 is formed by bending a plastic or metal rod into U-shaped form thus providing a leg member 12 opposite a second leg member 14. Embedded in the member 10, or welded thereto, are metal flanges 16, there being at least two such flanges on each leg. The flanges are preferably molded in the U-shaped member. Each flange 16 has a rather narrow base and an enlarged head so that casting material can flow between the enlarged head and the legs 12 and 14. As best shown in FIG. 3 the flanges 16 may also include outer portions which are bent at right angles to render the anchoring function more secure. Thus the member 10 is securely anchored to the casting material.

Figure 2:
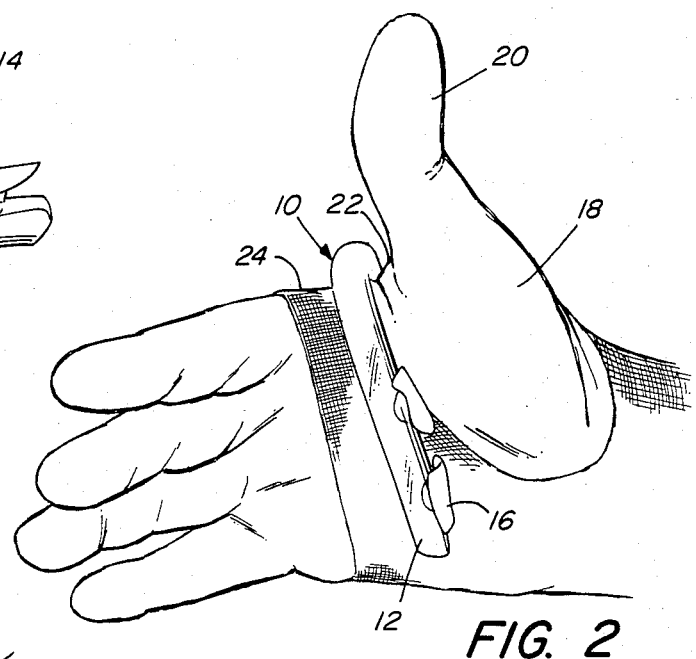
FIG. 2 is a view in perspective showing the U-shaped member in place on the hand of a patient after the initial bandage has been applied.

As shown in FIGS. 2 and 3 the first step in the treatment after a fracture has been reduced is to apply a cloth bandage 24 to the inner portion of the hand 18 of the patient. Then the U-shaped member is inserted so that its base overlies the skin of the web 22 with the leg 12 traversing the palm area of the bandaged hand and the leg 14 extends over the back of the bandaged hand. The term "web" is the medical term for the crotch between the fingers of the hand 18 and the thumb 20.

Figure 5:
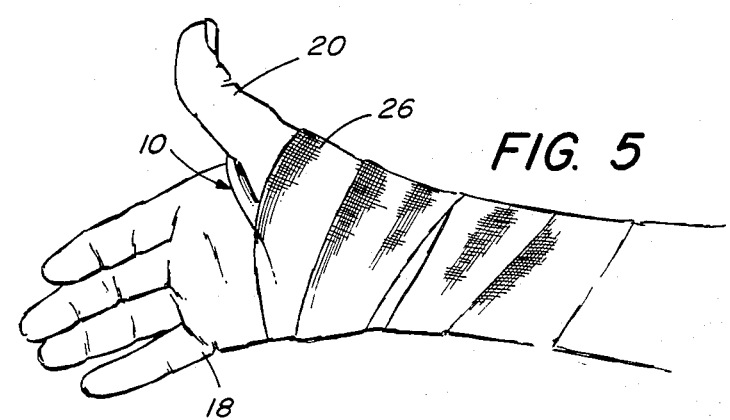
FIG. 5 is a view in perspective showing the U-shaped member in place after the casting material has been applied.

After the member 10 has been placed in position the next step is to apply casting material 26, generally plaster or fiber glass gauze, over the bandage 24 as shown in FIG. 5. The casting material(s) hardens around the flanges 16 and the traversing legs, embedding the web guard in the casting material(s). Consequently, the flanges not only serve to anchor the member 10 in proper position, but also serve to prevent the cast 26 from sliding toward the elbow, a situation which has been apt to happen when the swelling dies down.

Figure 6:
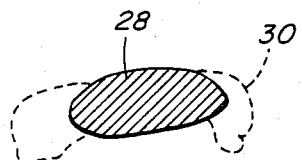
FIG. 6 is a view in cross-section through a U-shaped member having an oval cross-section and the dotted lines show a modification in which the cross-section is arcuate.

In FIGS. 1-5 the member 10 has been shown as cylindrical in cross-section, but the cross-section configuration is not at all critical. In FIG. 6 there is shown the cross-section 28 of an acceptable variation, the cross-section being oval and the surface being smooth. The dotted line 30 discloses another variation in which the cross-section is arcuate. Other cross-sections may occur to those skilled in the art.

The dimensions of the U-shaped member may vary in accordance with the size of the hand of the patient, and I contemplate that in practice there may be three sizes, —small, intermediate and large, but the differences in size will not be significant.

As explained and illustrated in "Orthopaedic Applicances Atlas," Vol. 1, J. W. Edwards—Ann Arbor, Michigan—1952, when a wrist or forearm has been fractured, it is customary to apply a plaster cast. Part of the cast, as the Atlas explains, "One thicker strip is used to complete the cast by crossing across the cleft of the thumb and the palm between thumb and distal palmar creases. This is made strong enough to stand the wear of work and narrow enough to allow freedom motion of the thumb and proximal finger joints." That has been the conventional technique. However, after a few days the web of the cast hand can become inflamed and sore. The portion of the cast upon the web of the hand has been required because the cast can slide upon the wrist and forearm, particularly when the usual swelling beneath the cast subsides. It is essential that the cast remain in place, and that is accomplished by the extension of the cast about the web of the hand. In other words, the smooth U-shaped guard not only prevents soreness and inflammation of the web of the hand, but securely anchors the cast in permanent position as long as it is in use.

The forward edge of the cast extends transversely from the base of the metacarpal phalange to the base of the thumb. Consequently, pronation of the hand as well as the wrist is prevented. The wrist is maintained in the desired splinted position. Moreover, the reduction in the area of the cast permits freer movement of the fingers and hand, thus resulting in less atrophy of the muscles in the forearm.

Having now described preferred embodiments of my invention, what I claim is as follows:

1. A method of protecting the web portion of a hand comprising the steps of prewrapping a bandage material about the hand, affixing to the hand a U-shaped member having one leg lying across the palm and extending upwards towards said web portion of the hand forming the arcuate section of said U-shaped member about the web portion and wherein a second leg extends downward from said arcuate portion across the backside of the hand, applying casting material to said hand such that the U-shaped member protects the skin of the web portion of said hand from the casting material thereby preventing irritation and inflammation.

2. A method of protecting the web portion of a hand comprising the steps of prewrapping a bandage material about the hand, affixing to the hand a smooth U-shaped member having one leg lying across the palm and extending upwards towards said web portion of the hand forming the arcuate section of said U-shaped member about the web portion and wherein a second leg extends downwards from said arcuate portion across the backside of the hand, applying casting material to said hand such that the U-shaped member protects the skin of the web portion of said hand from the casting material thereby preventing irritation and inflammation, the forward edge of the cast extending transversely from the base of the metacarpal phalange to the base of the thumb.

* * * * *